(12) United States Patent
Lundborg

(10) Patent No.: US 6,342,076 B1
(45) Date of Patent: Jan. 29, 2002

(54) PROSTHETIC DEVICE FOR JOINTS

(75) Inventor: Göran Lundborg, Genarp (SE)

(73) Assignee: Handevelop AB, Genarp (SE)

( * ) Notice: Subject to any disclaimer, the term of this patent is extended or adjusted under 35 U.S.C. 154(b) by 0 days.

(21) Appl. No.: 09/116,262

(22) Filed: Jul. 16, 1998

Related U.S. Application Data

(63) Continuation of application No. PCT/SE97/00093, filed on Jan. 22, 1997.

(30) Foreign Application Priority Data

Jan. 22, 1996 (SE) .................................................. 9600220

(51) Int. Cl.[7] .................................................... A61F 2/42
(52) U.S. Cl. .................................. 623/21.15; 623/21.11
(58) Field of Search ............................... 623/17, 18, 21, 623/20, 21.11, 21.12, 21.14, 21.15

(56) References Cited

U.S. PATENT DOCUMENTS 3,990,116 A     11/1976  Fixel et al.
4,092,740 A  *   6/1978  Eshriqui ...................... 623/21
4,309,777 A  *   1/1982  Patil .......................... 623/17
4,634,445 A      1/1987  Helal
5,171,284 A  * 12/1992  Branemark .................. 623/21
5,306,310 A  *   4/1994  Siebels ....................... 623/17
5,458,642 A  * 10/1995  Beer et al. .................. 623/17
5,507,812 A  *   4/1996  Moore ......................... 623/13
5,534,033 A  *   7/1996  Simpson ...................... 623/18

FOREIGN PATENT DOCUMENTS

| EP | 0057597 | 8/1982 |
| EP | 0454645 A1 | 10/1991 |
| SE | 8903838-4 | 7/1991 |
| WO | 91/07149 | 5/1991 |
| WO | 91/16014 | 10/1991 |
| WO | 94/11606 | 5/1994 |

* cited by examiner

Primary Examiner—Bruce Snow
(74) Attorney, Agent, or Firm—Burns, Doane, Swecker & Mathis, L.L.P.

(57) ABSTRACT

In a prosthetic device for joints for implantation in humans and animals, a joint body is arranged between two fixing elements which are intended to be connected to adjoining bone parts. The joint body includes at least one essentially helical spring, and the ends of each spring are connected to the fixing elements.

20 Claims, 3 Drawing Sheets

PROSTHETIC DEVICE FOR JOINTS

This is a continuation of International Application No. PCT/SE97/00093, filed Jan. 22, 1997, that designates the United States of America.

The present inventions relates to a prosthetic device for joints for implantation in humans and animals, the device comprising a joint body arranged between two fixing elements which are adapted to be connected to adjoining bone parts.

BACKGROUND OF THE INVENTION

Several diseases cause destruction of joints, resulting in chronic pain and impaired movability. The problem is most pronounced in patients who suffer from chronic rheumatoid arthritis, but is also pronounced in, for instance, osteoarthritis (wear of cartilage) and in articular cartilage injuries after fractures and bacterial infections. In many of these cases the diseased and injured joint is replaced by an artificial joint structure.

However, experience has shown that too great an ambition to completely imitate the function of a normal joint in many cases results in failure. The artificial joint will easily be too complicated. For a rheumatic who has no joint function at all in, for instance, a hand, it is not necessary to aim at regaining a fully normal joint function via a prosthetic operation. The aim should instead be to obtain a painless joint with stability and a certain amount of movability, which makes the hand usable. Thus, the aim of the join structure must always be related to the patient's needs.

The main difficulties when constructing artificial joints in e.g. hands have been (1) to provide an artificial joint with satisfactory properties and (2) to fix the artificial joint to adjoining bones in a satisfactory manner.

The artificial joint may be of a fairly simple design, for instance a flexible, integral silicone body which resists a certain degree of deformation. However, such a structure does not claim to imitate the structure of a normal joint, but instead a structure is desired, which is as simple as possible. The advantage of such a structure is above all the stability in the system and the inherent resilience. The great drawback, however, is limited mechanical strength and a tendency of the silicone towards unfavourable local tissue reactions.

More complicated artificial joints are as a rule based on some sort of artificial articular head in an artificial joint cavity, for instance in the form of a two-component device. The advantage of such a structure is that the movement pattern largely imitates the normal movement pattern of a joint and that a number of suitable biomaterials are available, inter alia by experience from knee and hip prostheses (for instance polyethylene, titanium, vitallium). Serious drawbacks of such structures are, however, the risk of wear products forming owing to friction, and the complexity of the structure, which in many cases results in undesired tissue ingrowth in the system. Moreover, some sort of mechanical motion rod is required to hold the two joint components together. Besides, there is no resilience at all in such a structure, which is a serious drawback in e.g. rheumatoid arthritis and similar states where the stretching tendons in many cases are considerably weakened.

There are two known main principles of fixing artificial joints to adjoining bones. According to one principle, no fixed anchoring is desired at all, but the shaft of the artificial joint is allowed to move back and forth in the marrow cavities of the adjoining bones, for instance when moving a hand and fingers. The advantage of this principle is that the movements in the artificial joint structure are spread over a long distance, and that the strain to which the material is subjected is thus reduced. A drawback is above all extensive foreign body reactions owing to movements and wear in the foreign material. This leads to the bone becoming thinner and increasing stiffness. Besides, fractures are common in the frequently used silicone, and the reconstructed joint easily becomes stiff.

According to the other principle for anchoring the artificial joint structure to adjoining bones, a fixed anchoring is desired. This was earlier effected by means of cement. However this principle suffers from serious drawbacks. For instance, in the case of hands, the bones therein have insufficient tolerance for heat development and toxic products from the cement, which has given disastrous results. A solution to this problem may be the cement-free so-called osseointegration principle which was introduced by professor BrAnemark. According to this principle, the anchoring elements are titanium screws which are inserted into the bone parts of the joint and there grow together with the bone, whereby the screws constitute permanent fixing points. The advantage of this technique is the absence of unfavourable tissue reactions and a probably permanent anchoring of the screws in the bone. Thus there are today satisfactory solutions to the previous problem of fixing artificial joints.

In plastic surgery of joints (arthroplasty) in e.g. hand surgery, use is today made of a limited number of methods based on different principles in respect of joint structure as well as fixing of the joint structure to adjoining bones. The most common method, Swanson's silicone arthroplasty, is based on the first of the abovementioned principles of fixing. A solid body of silicone with two longitudinal shafts projecting in opposite directions from a flexible intermediate part replaces the diseased joint. The shafts are inserted in the marrow cavities of the long bone on both sides of the reconstructed joint. As mentioned above, the system, however, suffers from considerable drawbacks. The complications which in recent years have been described in connection with the use of silicone material as breast implants have resulted in this technique being seriously questioned, and its popularity seems to decrease more and more. The method definitely cannot be used on young rheumatics with an expected long length of life.

Another method used is based on a two-component device having an articular head in a joint cavity, and this device is fixedly anchored to adjoining bones. Attempts have been made to provide such anchoring by means of cement (for instance the St George technique). However, these attempts have not been successful in hand surgery since cement, owing to its heat development and toxicity, has resulted in tissue death and stiffness. The absence of resilience in the system besides results in bending contractures. Dislocations (luxations) are common since the articular head and the joint cavity easily slide apart. This technique is no longer in clinical use for reconstruction of finger joints. For wrist reconstruction, the method is of a certain value, but owing to increasing stiffness and tendency towards coming loose in the patient, the technique is not at all used in Sweden.

According to a further, more biologically oriented method, fixed anchoring points for the joint structure in the bone are established by means of the above-mentioned osseointegration method by inserting titanium screws (ad modum Branemark) into the bone tissue. Clinical experience shows that such screws remain immovable and fixedly anchored in the bone tissue. The advantage of this method is, inter alia, the absence of movable foreign material in the marrow cavities of the bones. In clinical application, use has up to now been made of a simple joint structure consisting of a solid body of flexible silicone. The movability of the joint structure thus is used in its entirety in that part of the structure which is located between the anchoring elements, i.e. the silicone component. The drawback of this method is that the stress to which this component is subjected will thus be very great, involving a risk of fatigue and damage to the silicone material. Fractures in the silicone material have been reported, and therefore the structure has not been considered sufficiently strong to allow introduction for general clinical use.

A further problem is to be found in the treatment of patients suffering from so-called thumb base osteoarthrosis in the wrist. This state involves osteoarthrosis, i.e. cartilage destruction, in the joint between the first metacarpal bone and the trapezoid bone (trapezium), optionally also between the trapezoid bone and navicular bone (scaphoideum). In this treatment, the trapezoid bone is usually removed and replaced by an interposed loop from an adjoining tendon. This treatment always results in a certain shortening in the system, and the clinical result varies too much to be quite satisfactory. In another method of treatment, the trapezoid bone is replaced by a silicone prosthesis, which is attached to the first metacarpal bone by means of a shaft inserted in the marrow cavity of the bone. Also this method of treatment, however, suffers from considerable drawbacks, among other things a tendency towards luxation of the prosthesis since there is no fixing to the navicular bone. Thus, for treating thumb base osteoarthrosis, no satisfactory replacement material is available.

WO 94/11606 (Chene et al) discloses an artificial joint system with two rigid components which can move relative to each other in a simple hinge mechanism. Inside the two components there are longitudinal channels which contain flexible elements, one in the form of a rod-shaped device extending through the two rigid components, and one being a helical spring at the far end of the one rigid component. This system allows movements in one plane only, which is moderated by the elasticity of the spring. The joint component in this structure is a hinge, whose mechanical properties are affected by the helical spring positioned at a distance from the hinge. This rigid system allows neither lateral deviations nor a shock-absorbing effect.

EP-A-O 454 645 (Medevelop AB) discloses an artificial joint mechanism which is entirely based on a solid body of thermoplastic adapted to be attached to fixed anchoring elements on each side of the joint structure. The joint body can be reinforced in various ways by means of longitudinal fibres, plates or netting structures. In one variant, use is made of an outer longitudinal helical spring, which serves only as reinforcement of the actual thermoplastic body and has no direct connection with the opposite bone part. In another embodiment, a helical spring with a diameter tapering in the direction of the attachment in one adjoining bone part is fitted in the thermoplastic joint body. However, the spring has no direct connection with the opposite bone part and is only intended to serve as an inner reinforcing complement to the solid joint body.

Swedish Patent Specification 8903838-4 (Volvo AB) discloses a finger joint prosthesis where at least one helical spring extending transversely of the direction of the joint constitutes the actual joint structure. The structure is of the "clothes-peg" type and is adapted to be attached to fixed anchoring elements on each side of the structure. The system yields satisfactory resilience, but there is no shock-absorbing effect and no possibility of lateral deviation and rotation in the system.

U.S. Pat. Specification 3,990,116 discloses a leaf spring structure, the longitudinal elements of which are, via shafts, fixed to the adjoining bones. The system can be enclosed in various types of artificial capsules. The joint structure permits movements in a single plane with resilience. However, the system has no shock-absorbing effect, and no capability of lateral deviation or rotation. Moreover, the friction between the spring leaves causes a risk of harmful wear products appearing.

Summing up, the existing prosthetic devices for joints suffer from a number of drawbacks, and there is a great need of replacement materials that satisfy all the desired requirements for stability, resilience, shock-absorbance, resistance to wear, sufficient capability of lateral deviation and rotation and a simple design.

OBJECT OF THE INVENTION

The object of the present invention is to obviate the above-mentioned drawbacks that are associated with artificial prosthetic devices for joints that are available today.

This object is achieved by a prosthetic device for joints of the type mentioned by way of introduction, which has the features stated in the characterising clause of claim 1. Further features are defined in the subclaims.

SUMMARY OF THE INVENTION

The present invention will be described in more detail below, inter alia, with reference to the drawings.

The main principle of the present invention is to use one or more spring means as replacement material for joints, and also for certain bones in the human body. The inventive prosthetic device for joints can, of course, also be applied to certain animals, if desired and if possible.

The present invention is particularly applicable to reconstruction of the knuckle joints (MCP joints), the intermediate and outer joints of the fingers (PIP and DIP joints) and the wrist. The invention can also be used in thumb base osteoarthrosis as bone replacement for the trapezoid bone or as artificial joint between the first metacarpal bone and the trapezoid bone and/or between the trapezoid and the navicular bone. The invention can also be used as bone replacement for intervertebral discs or individual vertebrae in the spinal column. The present invention is, of course, also applicable to other similar joint and bone systems in the body, also where replacement structures are now rare, but which may be of interest in future, for instance in the joints of the foot.

The inventive prosthetic device for joints comprises a joint body arranged between two fixing elements, the joint body comprising at least one essentially helical spring means, and the ends of the spring means being connected to the fixing elements.

By the expression "essentially helical" spring means is meant a helical spring having at least one winding and a structure where minor deviations from the helical shape may occur, without affecting the properties of the spring in an undesired manner.

By the expression "longitudinal direction of the joint body", which is below used throughout, is meant the axial direction in which the joint and its adjoining bone parts extend in stretched condition. Small deviations in the longitudinal direction of the joint body and, thus, the spring means may of course occur and are comprised in the scope of protection of the present application. Spring means, whose longitudinal direction deviates too much, are as a rule unusable, for instance in the extreme case of transverse springs.

Figure 1:
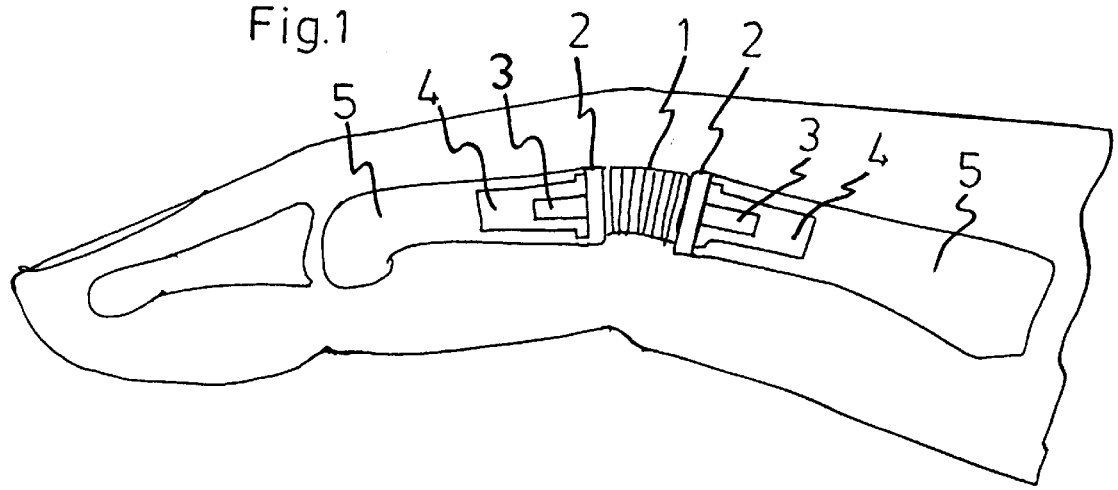
FIG. 1 illustrates an embodiment of the present invention for a finger joint.

FIG. 1 is a side view of a preferred embodiment of a prosthetic device for joints in the intermediate finger joint with one joint body 1 of two parallel cylindrical springs arranged in a plane perpendicular to the plane of bending of the joint body 1 and the finger. These two springs are, at each end, via a base plate 2 and a fixing means 3 fixed to anchoring means 4 in adjoining bone parts 5.

Figure 2A:
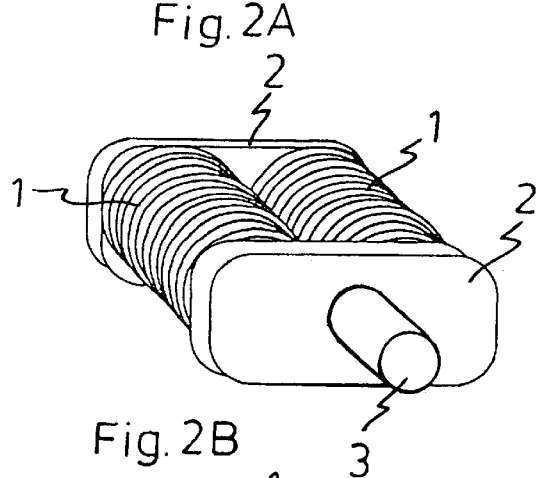
FIGS. 2A–D are different views of the device in FIG. 1.
Figure 2B:
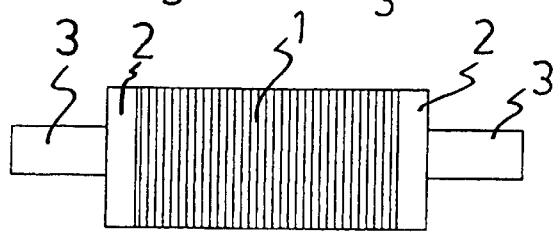
Figure 2C:
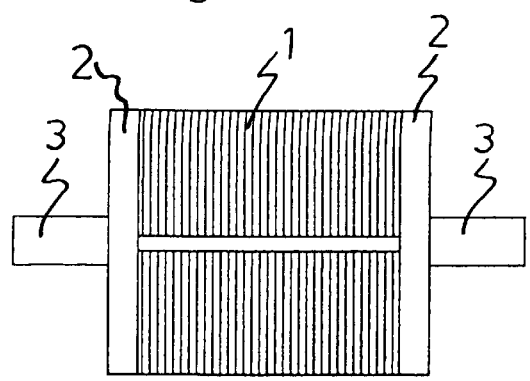
Figure 2D:
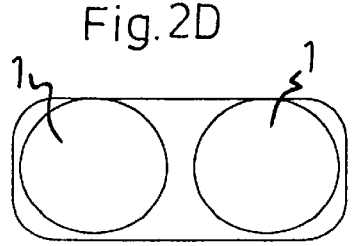
Figure 3A:
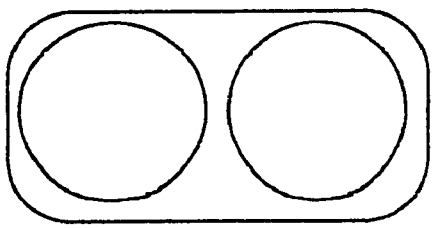
FIGS. 3A–H are cross-sectional views of various embodiments of the prosthetic device for joints according to the present invention.
Figure 3B:
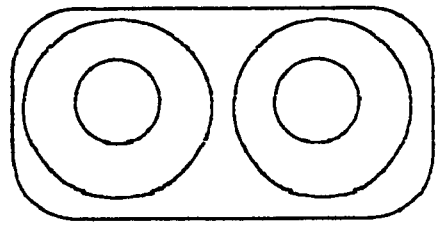
Figure 3C:
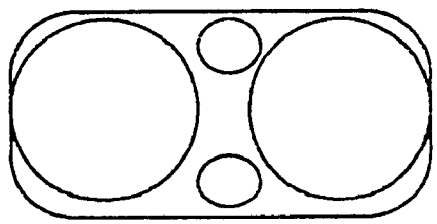
Figure 3D:
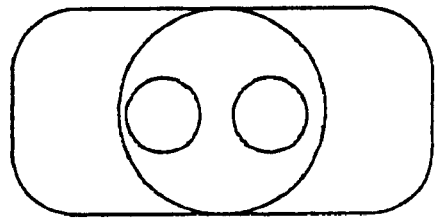
Figure 3E:
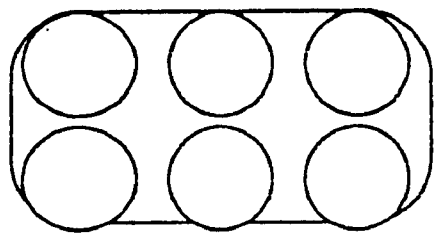
Figure 3F:
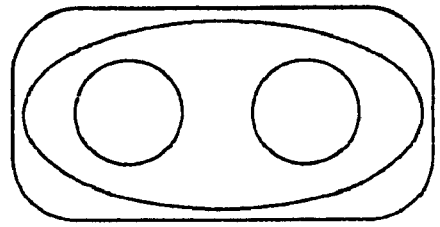
Figure 3G:
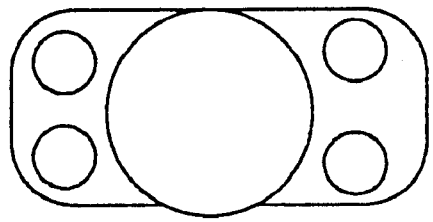
Figure 3H:
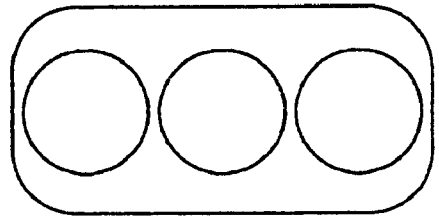

FIGS. 2A–D illustrate in detail the joint body 1 shown in FIG. 1. The perspective view in FIG. 2A shows the two parallel spring means, the base plates 2 and the fixing means 3. In FIGS. 2B–D, the prosthetic device is shown from the side, from above and in cross-section in the longitudinal direction of the joint body 1.

According to the inventive idea, use is made of one or more spring means as supporting joint body 1 in the prosthetic device. Optimum stability is usually obtained when using a plurality of spring means, but use of a single, suitably designed spring may also give a satisfactory result. The expression "spring means", which is used throughout the specification, thus is intended to comprise also the embodiment having a single spring means, unless otherwise stated.

The prosthetic device for joints according to the present invention, i.e. the spring means, the base plates 2 and the fixing means 3, can be made of any biocompatible material/s that are suitable and approved for implantation, e.g. titanium or stainless steel. The wires of the spring means can, for instance, also be covered with a suitable biological material to increase their biocompatibility. In this way, problems of inflammation or rejection after implantation are obviated.

In the present invention, in contrast to prior-art prosthetic structures, the actual spring means constitute a deformable joint body 1. The joint body 1 according to the present invention thus is of a considerably simpler design than the prior-art joint bodies, i.e. it is considerably less complicated in terms of construction, thereby rendering the manufacture thereof easier. For example, the length of the joint body can be easily varied by being cut off. Moreover, also the possibility of formation of wear products is minimised. The spring means also permit movements in one or more planes, resilience in bending movements and a shock-absorbing effect in case of axial compression. A certain desired degree of lateral deviation and rotation of the joint body is also made possible. This combination of desired properties is not to be found in any of the prosthetic devices for joints that are available today.

The purpose of the design of the joint body 1 according to the invention is in the first place to distribute, over a long distance, the deformation in the joint body induced by bending movements although the movement per se must be contained within the short distance that corresponds to the normal extent of the joint. As a result, the risk of the material being damaged is reduced. A large movement in the artificial joint is "geared down" to a large number of small movements over the entire length of the helical springs. For instance, a helical spring having a diameter of 5 mm and a length of 10 mm can easily contain 300 mm wound material and all the same offer resilience, stability and flexibility suitable for the purpose. By the fact that the spring means per se constitute the supporting, flexible and stabilising basic structure of the joint body 1, the need of a further deformable supporting joint body, e.g. of polymer material, is eliminated.

Each spring means can be attached to the base plate 2 in any conventional manner that affords the joint body 1 sufficient stability and durability. The spring means in the joint body 1 can be attached to the base plate 2 by means of a weld seam, by gluing or by the ends of the windings of the spring means being "screwed" over the base plate 2 and locked in position, for instance by means of a groove or a recess in the plate. The windings of the spring means closest to the associated base plate 2 can also be supported from inside by a tight fit of e.g. a short structure protruding from the base plate 2, for instance a cylindrical structure. These methods of attachment and other similar methods can be used separately or in combination.

The base plates 2 are adapted to be connected, via the fixing means 3, to fixed anchoring means 4 inserted in adjoining bone parts 5 on each side of the prosthetic device for joints. Several conventional, suitable methods for attachment are available. An established method means, as mentioned above, that the fixing means 3 in the form of shafts, which protrude from the base plates 2, are inserted in longitudinal channels in the longitudinal direction of the anchoring means 4. The anchoring means 4 can be made of ceramic material, titanium or some other substance having suitable biological and mechanical properties.

Depending on the position in the body, where the helical springs are to be used as joint body 1, they can be tension springs or compression springs, both being examples of helical springs. A tension spring is closely wound and affords good lateral stability in the system and resistance when tensioned. Such a tight cylindrical structure induces, after implantation in a biological tissue, the formation of a thin outer tissue membrane around the helical spring, i.e. some kind of physiological encapsulation. Tension springs do not allow any further compression in the system, but yield satisfactory stability and resilience in case of lateral wobbling.

A compression spring, on the other hand, is less closely wound than a tension spring, and the windings are not in immediate contact with each other. This type of spring affords, in addition to resistance when tensioned, also a shock-absorbing effect in case of axial compression. Compression springs also result in satisfactory stability and resilience.

The term "spring means" has for the sake of simplicity been replaced by the term "spring" or "springs" in the rest of the specification.

Figure 4A:
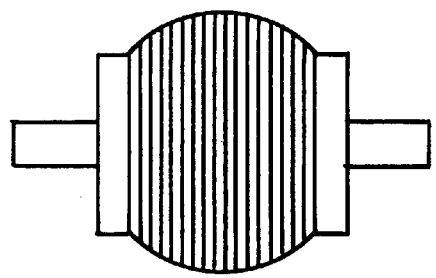
FIGS. 4A–D illustrate further embodiments of the prosthetic device for joints.
Figure 4B:
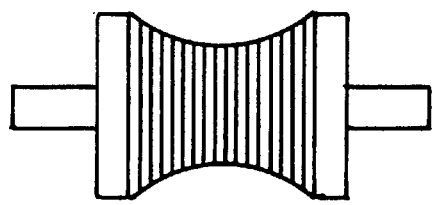

The prosthetic device for joints according to the present invention can be of different embodiments, depending on the position in the body, where they are to be implanted and how they are intended to function. Thus, a number of similar or different, essentially parallel springs can be used in combination, one or more of the springs differing from the others, and/or each varying in itself in respect of winding cross-section, pitch, pitch angle and/or wire cross-section. One or more springs can also be essentially concentrically arranged inside one or more bigger springs, or be inserted into each other according to a principle similar to that of e.g. a DNA molecule. By the expressions "essentially parallel" and "essentially concentric" are meant that a small deviation in the longitudinal direction between different spring means is comprised in the scope of protection of the invention. Furthermore, both tension and compression springs can be used in one and the same prosthetic device for joints. The springs are in their longitudinal directions preferably cylindrical, but can also be convex or concave, as shown in FIGS. 4A and 4B. Below follows a detailed description of various embodiments of the prosthetic device for joints according to the present invention.

Joint Body with a Varying Number of Springs

Two or more parallel springs arranged in a plane which is perpendicular to the plane of bending of the joint body 1 give good lateral stability and retained satisfactory movability in one plane (see e.g. the embodiment in FIGS. 2A–D). When reconstructing a joint, both bending and stretching are thus made possible, as well as a certain amount of restricted lateral deviation. Such a joint body 1 is particularly suitable for reconstruction of the knuckle joints (MPC joints) and the intermediate joints of the fingers (PIP joints).

Joint Body with a Combination of Tension and Compression Springs

By combining tension and compression springs, the stability of the joint body 1 can be modified in various ways. By arranging, for example, two or more parallel compression springs adjacent to one or more tension springs, the lateral deviation of the joint body can be modified and controlled in a physiologically and mechanically advantageous manner. Such a structure is especially well suited in arthroplasty in the wrist.

Joint Body with a Varying Number of Springs and a Varying Positioning thereof

By varying the positions of the springs on each base plate 2, the mechanical properties of the prosthetic device for joints can be modified and controlled. As appears from FIGS. 3A–H, which illustrate various embodiments in cross-section in the longitudinal direction of the joint body 1, helical springs of varying diameter and structure, for instance both tension and compression springs, can be combined in various ways, as required. For example, one or more springs can be located inside one or more bigger springs or in other suitable positions. More than two springs in the joint body cause increased reliability if one of the springs-should break.

Joint Body having a Varying Section of the Spring Wire

The mechanical and biological properties of the springs can be varied by varying the section of the wire. Its cross-section can be e.g. round, oval, transverse or inclined in different planes.

Joint Body with Springs of Varying Length

The length of the springs can be varied as required. In small joints, for instance in the intermediate and outer joints of the fingers, it is usually advantageous to have very "short" springs.

Joint Body with Springs having a Varying Winding Diameter

The winding diameter of the springs can, like in conical helical springs, be varied in different ways along the length of the spring, which is evident from FIGS. 4A and B. The spring can be, for instance, convex ("egg-shaped") with its greatest diameter in the centre, such as in FIG. 4A, or concave ("hour-glass-shaped") with its smallest diameter in the centre, as in FIG. 4B. In this way, the winding of the springs when bent and stretched can be displaced in relation to each other in a manner that is not possible with a common cylindrical spring, which may be desirable in certain applications.

Figure 4C:
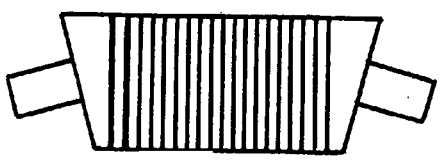
Figure 4D:
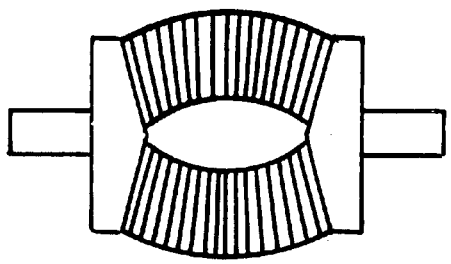

As mentioned above, the base plate 2 in the prosthetic device for joints according to the present invention can be made of any suitable biocompatible material whatever. The design of the base plate 2 is not critical for the present invention, but it may be of any suitable plate shape. However, that surface of the base plate 2 which is directed to the joint body 1 can be, for instance, angled in relation to the longitudinal direction of the joint body 1, which appears from the side view in FIG. 4C. In this manner, the starting position of movements in the prosthetic device for joints can be varied, which can be of importance in finger joint reconstructions, where priority is given to a satisfactory bending capability instead of a satisfactory stretching capability. Moreover, the surface which is directed to the joint body 1 of a base plate 2 for two springs can be angled as shown in FIG. 4D, where an embodiment is illustrated from above, i.e. such that the springs, which are arranged in a plane perpendicular to the plane of bending of the joint body 1, in the resting position in the longitudinal direction of the joint body 1 form arcs curved away from each other. Such a design results in even and smooth lateral stability in the joint body 1. If required, the base plate 2 can also be designed such that more than two springs form arcs in the resting position.

After implantation of a prosthetic device for joints according to the present invention, a thin capsule consisting of a connective tissue membrane automatically forms, as mentioned above, around each spring. This phenomenon is most pronounced when a closely wound tension spring is used, and is less developed when using a compression spring with a less close winding. If necessary, each spring can be provided with an artificial outer capsule for the purpose of minimising undesired tissue ingrowth in the system. Such a capsule may consist of a thin membrane of a woven or homogeneously deformable material with suitable biological and mechanical properties. The membrane can be resorbable or not.

When using a compression spring, this can be enclosed by e.g. a net-shaped nonyieldable capsule for the purpose of limiting and affecting the displacements of the windings in case of movements in the system. When bending such a spring, no widening takes place between the windings on the "upper side" of the spring. Displacement of the windings of the spring towards each other is possible only on the "underside".

The joint body 1 in its entirety can be encapsulated with a surrounding casing having a very close winding and a configuration (e.g. oval or rectangular) which permits enclosure of the joint body 1 itself. When designing such a "capsule", priority is given to the "membrane effect" instead of mechanical strength. When using a closely wound thin wire, a most insignificant widening between the windings of the spring thus takes place, also in case of large movements in the system. In this fashion, two different types of spring may supplement one another in a favourable way, i.e. a system of interior springs which are responsible for the mechanical properties of the structure, supplemented with an exterior enclosing spring system which is essentially directed to a barrier effect. These two spring systems should be made of a material having suitable biological and mechanical properties.

The forming of an outer biological membrane around one or more springs in the joint body is facilitated by the spring or springs, before implantation, surrounding a tube of a biocompatible, optionally resorbable material, said tube, however, not constituting a supporting body for the prosthetic device for joints. In this way, a biological capsule forms automatically around the spring after implantation.

By selecting a suitable size and configuration of the springs included in the joint body, the contour of the normal articular head can be imitated in a cosmetically advantageous fashion.

The dimensions of the components of the prosthetic device for joints are not restricted, but of course vary depending on the dimensions of the joint or bone part that is to be replaced in the human or animal at issue. In one embodiment of the prosthetic device for joints as illustrated in FIGS. 2A–D, each helical spring has a length of about 9 mm, a winding diameter of about 5 mm and a wire diameter of about 0.3 mm. The base plate 2 has a thickness of about 1 mm, a length of about 12 mm and a width of about 6 mm. The fixing means 3 has a diameter of about 2 mm and projects about 6 mm from the base plate.

Moreover, one or more springs of a suitable size and structure can be used as replacement for individual bones in the body. This principle is especially applicable to the wrist in so-called thumb base osteoarthrosis. As mentioned above, there is at present no quite satisfactory treatment of thumb base osteoarthrosis. A prosthetic device for joints according to the present invention can, however, replace the extirpated bone at issue, i.e. the trapezoid bone, in a considerably better manner than prior-art replacement materials. The spring gives a retained length in the system, while the possibility of movements in several planes is maintained. The spring an be fixed in anchoring points in adjoining bones as described above.

In the spinal column, there may be a need of replacing intervertebral discs or individual discs in various diseases. Also in this case, a prosthetic device for joints having a suitable size and design may constitute a satisfactory replacement material.

What is claimed is:

1. A prosthetic device as a replacement for knuckle joints, intermediate and outer joints of fingers, and wrist joints of the fingers and hands for implantation in humans and animals, the device comprising:
    two fixing elements which are each adapted to be connected to adjoining bone parts; and
    a joint body arranged between the two fixing elements, the joint body consisting essentially of two essentially helical springs, each essentially helical spring having opposite ends and extending in a longitudinal direction of the joint body, the opposite ends of each of the two essentially helical springs being connected to the fixing elements,
    wherein at least one of interference between the two essentially helical springs and tension in the two essentially helical springs limits the joint body to bending substantially only in a single plane.

2. A prosthetic device as claimed in claim 1, wherein the two essentially helical springs differ from each other in respect of one or more of length, winding cross-section, pitch, pitch angle, and wire cross-section.

3. A prosthetic device for joints as claimed in claim 2, wherein one or more of the two essentially helical springs is at least one of convex and concave in its longitudinal direction.

4. A prosthetic device for joints as claimed in claim 2, wherein the joint body consists essentially of two parallel cylindrical springs in a plane extending perpendicular to a plane of bending of the joint body.

5. A prosthetic device for joints as claimed in claim 1, wherein each spring is one of a tension spring and a compression spring.

6. A prosthetic device for joints as claimed in claim 5, wherein one or more of the two essentially helical springs is at least one of convex and concave in its longitudinal direction.

7. A prosthetic device for joints as claimed in claim 5, wherein the joint body consists essentially of two parallel cylindrical springs in a plane extending perpendicular to a plane of bending of the joint body.

8. A prosthetic device for joints as claimed in claim 1, wherein one or more of the two essentially helical springs is cylindrical in its longitudinal direction.

9. A prosthetic device for joints as claimed in claim 8, wherein the joint body consists essentially of two parallel cylindrical springs in a plane extending perpendicular to a plane of bending of the joint body.

10. A prosthetic device for joints as claimed in claim 1, wherein one or more of the two essentially helical springs is at least one of convex and concave in its longitudinal direction.

11. A prosthetic device as claimed in claim 1, wherein one of the two essentially helical springs is essentially concentrically arranged inside a bigger one of the two essentially helical springs.

12. A prosthetic device as claimed in claim 1, wherein one or more of the two essentially helical springs has a wire surface coated with a biocompatible material.

13. A prosthetic device for joints as claimed in claim 1, wherein the joint body extends between and joins the two fixing elements, and each fixing element includes a base plate arranged in a plane extending essentially perpendicular to the longitudinal direction of the joint body, the base plate having a surface connected to one end of the joint body, and a fixing means connected to surface of the base plate opposite the surface to which the joint body is connected, the fixing means projecting essentially in the longitudinal direction of the joint body, the fixing means being adapted to be connected to an anchoring means in an adjoining bone part.

14. A prosthetic device for joints as claimed in claim 8, wherein the surface of the base plate which is connected to the joint body is designed such that the two essentially helical springs, when in a resting position, are arcuate in the longitudinal direction of the joint body.

15. A prosthetic device for joints as claimed in claim 8, wherein fixing means projects from the base plate at an angle in relation to the longitudinal direction of the joint body.

16. A prosthetic device for joints as claimed in claim 8, wherein each of the two essentially helical springs has windings, the windings of each spring closest to an associated base plate being supported by a structure projecting from the base plate.

17. A prosthetic device for joints as claimed in claim 1, wherein the joint body consists essentially of two parallel cylindrical springs in a plane extending perpendicular to a plane of bending of the joint body.

18. A prosthetic device for joints as claimed in claim 1, wherein the joint body includes a combination of tension and compression springs.

19. A prosthetic device for joints as claimed in claim 1, wherein one or more of the two essentially helical springs is enclosed by a biocompatible material.

20. A prosthetic device for joints as claimed in claim 1, wherein the joint body consists essentially of the two essentially helical springs arranged substantially parallel to one another and extending in a longitudinal direction of the joint body, ends of each spring being connected to the fixing elements.

* * * * *